United States Patent
Glaesner et al.

(10) Patent No.: US 7,576,190 B2
(45) Date of Patent: Aug. 18, 2009

(54) FGF-21 FUSION PROTEINS

(75) Inventors: Wolfgang Glaesner, Indianapolis, IN (US); Rohn Lee Millican, Jr., Indianapolis, IN (US); Yu Tian, Carmel, IN (US); Sheng-Hung Rainbow Tschang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 199 days.

(21) Appl. No.: 11/578,614

(22) PCT Filed: May 2, 2005

(86) PCT No.: PCT/US2005/015111

§ 371 (c)(1),
(2), (4) Date: Oct. 16, 2006

(87) PCT Pub. No.: WO2005/113606

PCT Pub. Date: Dec. 1, 2005

(65) Prior Publication Data

US 2007/0237768 A1 Oct. 11, 2007

Related U.S. Application Data

(60) Provisional application No. 60/570,908, filed on May 13, 2004.

(51) Int. Cl.
C07K 16/00 (2006.01)
C07K 14/435 (2006.01)
C07K 14/50 (2006.01)
C07K 14/76 (2006.01)
C12P 21/04 (2006.01)

(52) U.S. Cl. .............. 530/399; 530/350; 530/380; 530/387.1; 435/69.7

(58) Field of Classification Search .............. None
See application file for complete search history.

(56) References Cited

U.S. PATENT DOCUMENTS 7,259,248 B2 * 8/2007 Itoh et al. ............. 530/399
7,271,149 B2 * 9/2007 Glaesner et al. ............. 514/12

FOREIGN PATENT DOCUMENTS

| WO | WO 96/04388 | 2/1996 |
| WO | WO 01/18172 | 3/2001 |
| WO | WO 01/36640 | 5/2001 |
| WO | WO 01/72957 | 10/2001 |
| WO | WO 02/46227 | 6/2002 |
| WO | WO 2004/110472 | 12/2004 |

OTHER PUBLICATIONS

Angal, S., et al., "A Single Amino Acid Substitution Abolishes the Heterogeneity of Chimeric Mouse/Human (IGG4) Antibody", Molecular Immunology, Elmsford, NY, US, 30(1):105-108 (1993).
Dikov, M., et al., "A Functional Fibroblast Growth Factor-1 Immunoglobulin Fusion Protein", Journal of Biological Chemistry, 273(25):15811-15817 (1998).

* cited by examiner

Primary Examiner—Marianne P Allen
(74) Attorney, Agent, or Firm—Lynn D. Apelgren

(57) ABSTRACT

The invention provides specific FGF-21 compounds fused to specific IgG4-Fc or HSA derivatives resulting in fusion proteins that are biologically active with an extended elimination half-life and a slower clearance. These FGF-21 compound fusion proteins and compositions are useful in treating type 2 diabetes, obesity, and metabolic syndrome.

3 Claims, No Drawings

FGF-21 FUSION PROTEINS

This is the national phase application, under 35 USC 371, for PCT/US2005/015111, filed 2 May 2005, which, claims the benefit, under 35 USC 119(e), of U.S. provisional application 60/570,908, filed 13 May 2004.

FIELD OF THE INVENTION

The present invention relates to fibroblast growth factor 21 compounds fused to proteins that have the effect of extending the in vivo half-life of the polypeptides. These fusion proteins can be used to treat non-insulin dependent diabetes mellitus, obesity and metabolic syndrome.

BACKGROUND OF THE INVENTION

Fibroblast growth factors are large polypeptides widely expressed in developing and adult tissues (Baird et al., *Cancer Cells*, 3:239-243, 1991) and play crucial roles in multiple physiological functions including angiogenesis, mitogenesis, pattern formation, cellular differentiation, metabolic regulation and repair of tissue injury (McKeehan et al., *Prog. Nucleic Acid Res. Mol. Biol.* 59:135-176, 1998). According to the published literature, the FGF family now consists of twenty-two members (Reuss et al., *Cell Tissue Res.* 313:139-157 (2003)).

Fibroblast growth factor 21 (FGF-21) has been reported to be preferentially expressed in the liver and described as a treatment for ischemic vascular disease, wound healing, and diseases associated with loss of pulmonary, bronchia or alveolar cell function and numerous other disorders (Nishimura et al., *Biochimica et Biophysica Acta*, 1492:203-206, (2000); U.S. Pat. No. 6,716,626 and WO01/18172). More recently, FGF-21 has been shown to stimulate glucose-uptake in mouse 3T3-L1 adipocytes in the presence or absence of insulin, and to decrease fed and fasting blood glucose levels in ob/ob and db/db mice and 8 week old ZDF rats in a dose-dependant manner, thus, providing the basis for the use of FGF-21 as a therapy for treating type 2 diabetes and obesity (WO03/011213).

The present invention is based on the finding that the fusion of a protein with a long circulating half-life, such as the Fc portion or an immunoglobulin or albumin, to a FGF-21 compound results in a biologically active, FGF-21 fusion protein with an extended elimination half-life and reduced clearance when compared to that of native FGF-21.

The FGF-21 fusion proteins of the present invention have greater usefulness as a therapeutic as well as greater convenience of use than wild-type FGF-21 because they retain all or a portion of the biological activity of wild-type FGF-21 yet have an extended time action when compared to that of the wild-type FGF-21.

Therefore, FGF-21 fusion proteins of the present invention are useful to treat subjects with disorders including, but not limited to, type 2 diabetes, obesity, and metabolic syndrome, with particular advantages being that the FGF-21 fusion proteins of the present invention have improved efficacy due to constant exposure and require fewer doses, increasing both the convenience to a subject in need of such therapy and the likelihood of a subject's compliance with dosing requirements.

SUMMARY OF THE INVENTION

Compounds of the present invention include a heterologous fusion protein comprising a first polypeptide with a N-terminus and a C-terminus fused to a second polypeptide with a N-terminus and a C-terminus wherein the first polypeptide is a FGF-21 compound and the second polypeptide is selected from the group consisting of (a) the Fc portion of an immunoglobulin;

(b) an analog of the Fc portion of an immunoglobulin; and (c) fragments of the Fc portion of an immunoglobulin, and wherein the C-terminus of the first polypeptide is fused to the N-terminus of the second polypeptide via a linker or alternatively the N-terminus of the first polypeptide is fused to the C-terminus of the second polypeptide via a linker. It is preferred that the linker is selected from the group consisting of a peptide linker; a glycine rich peptide; and, a peptide having the sequence [Gly-Gly-Gly-Gly-Ser]$_n$ where n is 1, 1.5, 2, 3, 4, 5 or 6. Additional compounds of the present invention include a heterologous fusion protein comprising a first polypeptide with a N-terminus and a C-terminus fused to a second polypeptide with a N-terminus and a C-terminus wherein the first polypeptide is a FGF-21 compound and the second polypeptide is selected from the group consisting of a) human albumin;

b) human albumin analogs; and c) fragments of human albumin, and wherein the C-terminus of the first polypeptide is fused to the N-terminus of the second polypeptide or alternatively the N-terminus of the first polypeptide is fused to the C-terminus of the second polypeptide. The FGF-21 compound may be fused to the second polypeptide via a linker. It is preferred that the linker is selected from the group consisting of a peptide linker; a glycine rich peptide; and, a peptide having the sequence [Gly-Gly-Gly-Gly-Ser]$_n$ where n is 1, 1.5, 2, 3, 4, 5 or 6.

The present invention also includes polynucleotides encoding the heterologous fusion protein described herein, vectors comprising these polynucleotides and host cells transfected or transformed with the vectors described herein. Also included is a process for producing a heterologous fusion protein comprising the steps of transcribing and translating a polynucleotide described herein under conditions wherein the heterologous fusion protein is expressed in detectable amounts.

Another embodiment of the present invention encompasses pharmaceutical compositions of FGF-21 fusion proteins and methods of treating a patient suffering from type 2 diabetes, obesity, or metabolic syndrome comprising administering to said patient a therapeutically effective amount of a heterologous fusion protein described herein.

DETAILED DESCRIPTION OF THE INVENTION

For purposes of the present invention, as disclosed and claimed herein, the following terms are as defined below.

FGF-21 is a 208 amino acid polypeptide containing a 27 amino acid leader sequence. Human FGF-21 has ~79% amino acid identity to mouse FGF-21 and ~80% amino acid identity to rat FGF-21. Human FGF-21 or a mutein thereof is the preferred polypeptide template for the FGF-21 fusion proteins of the present invention but it is recognized that one with skill in the art could readily make fusion proteins based on an alternative mammalian FGF-21 polypeptide sequence.

The amino acid positions of the present invention are determined from the mature, wild type or native human 181 amino acid FGF-21 polypeptide as shown below (SEQ ID NO:1):

```
1                                       10                                      20
His Pro Ile Pro Asp Ser Ser Pro Leu Leu Gln Phe Gly Gly Gln Val Arg Gln Arg Tyr 30                                      40
Leu Tyr Thr Asp Asp Ala Gln Gln Thr Glu Ala His Leu Glu Ile Arg Glu Asp Gly Thr 50                                      60
Val Gly Gly Ala Ala Asp Gln Ser Pro Glu Ser Leu Leu Gln Leu Lys Ala Leu Lys Pro 70                                      80
Gly Val Ile Gln Ile Leu Gly Val Lys Thr Ser Arg Phe Leu Cys Gln Arg Pro Asp Gly 90                                      100
Ala Leu Tyr Gly Ser Leu His Phe Asp Pro Glu Ala Cys Ser Phe Arg Glu Leu Leu Leu 110                                     120
Glu Asp Gly Tyr Asn Val Tyr Gln Ser Glu Ala His Gly Leu Pro Leu His Leu Pro Gly 130                                     140
Asn Lys Ser Pro His Arg Asp Pro Ala Pro Arg Gly Pro Ala Arg Phe Leu Pro Leu Pro 150                                     160
Gly Leu Pro Pro Ala Leu Pro Glu Pro Pro Gly Ile Leu Ala Pro Gln Pro Pro Asp Val 170                                     180
Gly Ser Ser Asp Pro Leu Ser Met Val Gly Pro Ser Gln Gly Arg Ser Pro Ser Tyr Ala

Ser
```

The corresponding DNA sequence coding for the mature human 181 amino acid FGF-21 polypeptide is (SEQ ID NO:2):
CACCCCATCCCTGACTCCAGTCCTCTCCTGCAATTCGGGGGCCAAGTCCG

GCAGCGGTACCTCTACACAGATGATGCCCAGCAGACAGAAGCCCACCTGG

AGATCAGGGAGGATGGGACGGTGGGGGGCGCTGCTGACCAGAGCCCCGAA

AGTCTCCTGCAGCTGAAAGCCTTGAAGCCGGGAGTTATTCAAATCTTGGG

AGTCAAGACATCCAGGTTCCTGTGCCAGCGGCCAGATGGGGCCCTGTATG

GATCGCTCCACTTTGACCCTGAGGCCTGCAGCTTCCGGGAGCTGCTTCTT

GAGGACGGATACAATGTTTACCAGTCCGAAGCCCACGGCCTCCCGCTGCA

CCTGCCAGGGAACAAGTCCCCACACCGGGACCCTGCACCCCGAGGACCAG

CTCGCTTCCTGCCACTACCAGGCCTGCCCCCCGCACTCCCGGAGCCACCC

GGAATCCTGGCCCCCCAGCCCCCCGATGTGGGCTCCTCGGACCCTCTGAG

CATGGTGGGACCTTCCCAGGGCCGAAGCCCCAGCTACGCTTCC

The FGF-21 useful in the methods of the present invention is preferably a mutein, analog or derivative of human FGF-21 as shown in SEQ ID NO: 1, hereinafter collectively known as FGF-21 compounds. FGF-21 compounds have sufficient homology to FGF-21 such that the compounds have the ability to bind to the FGF-21 receptor and initiate a signal transduction pathway resulting in glucose uptake stimulation or other physiological effects as described herein. For example, FGF-21 compounds can be tested for glucose uptake activity using a cell-based assay such as that described in Example 1.

A "subject" or "patient" is a mammal, preferably a human.

Type 2 diabetes (non-insulin dependent diabetes mellitus (NIDDM)) is characterized by excess glucose production in spite of the availability of insulin, and circulating glucose levels remain excessively high as a result of inadequate glucose clearance.

Glucose intolerance can be defined as an exceptional sensitivity to glucose.

Hyperglycemia is defined as an excess of sugar (glucose) in the blood.

Hypoglycemia, also called low blood sugar, occurs when your blood glucose level drops too low to provide enough energy for your body's activities.

Hyperinsulinemia is defined as a higher-than-normal level of insulin in the blood.

Insulin resistance is defined as a state in which a normal amount of insulin produces a subnormal biologic response.

Metabolic syndrome can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and, blood pressure of 130/85 or higher.

Native or wild-type refers to the mature human 181 amino acid FGF-21 polypeptide as shown in SEQ ID NO:1. The term "native" or "wild-type" is intended to encompass allelic variants of the polypeptide in question.

The term "amino acid" is used herein in its broadest sense, and includes naturally occurring amino acids as well as non-naturally-occurring amino acids, including amino acid variants and derivatives. One skilled in the art will recognize, in view of this broad definition, that reference herein to an amino acid includes, for example, naturally occurring proteogenic L-amino acids; D-amino acids; chemically modified amino acids such as amino acid variants and derivatives; naturally occurring non-proteogenic amino acids such as norleucine, β-alanine, ornithine, etc.; and chemically synthesized compounds having properties known in the art to be characteristic of amino acids. Examples of non-naturally occurring amino acids include α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids) and amino acids in which a carboxylic acid functional group in the side chain is replaced with a sulfonic acid group (e.g., cysteic acid). Preferably, however, the FGF-21 compounds of the present invention comprise only naturally occurring amino acids except as otherwise specifically provided herein.

In the nomenclature used herein to designate FGF-21 compounds, amino acids are identified using the three-letter code or alternatively using the standard one letter code. Mutations are designated by the three-letter code for the original amino acid, followed by the amino acid number, followed by the three-letter code for the replacement amino acid. The numerical designations of each mutein is based on SEQ ID NO:1. For example, a substitution for leucine at position 118 (i.e. Leu118 or L118) with cysteine (Cys) is designated as Leu118Cys or L118C. In a similar fashion, the double substitution for isoleucine at position 152 and serine at position 163 (Ile152/Ser163) with the negatively charged amino acid, glutamate (Glu) is designated as Ile152Glu/Ser163Glu or I152E/S163E. "In vitro potency" as used herein, is the measure of glucose uptake of a FGF-21 fusion protein in a cell-based assay and is a measure of the biological potency of a FGF-21 compound. In vitro potency is expressed as the "$EC_{50}$" which is the effective concentration of compound that results in 50% activity in a single dose-response experiment. For the purposes of the present invention, in vitro potency is determined using a glucose uptake assay that employs 3T3-L1 cells (Example 1).

The term "plasma half-life" refers to the time in which half of the relevant molecules circulate in the plasma prior to being cleared. An alternatively used term is "elimination half-life." The terms "extended time action" or "longer time action" used in the context of plasma half-life or elimination half-life indicates there is a statistically significant increase in the half-life of a FGF-21 fusion protein relative to that of the reference molecule (e.g., the non-fusion form of the polypeptide or the native polypeptide) as determined under comparable conditions. Preferably a FGF-21 fusion protein of the present invention has an elimination half-life greater than that of a comparable FGF-21 compound. The half-life reported herein in Example 3 is the elimination half-life; it is that which corresponds to the terminal log-linear rate of elimination. Those of skill in the art appreciate that half-life is a derived parameter that changes as a function of both clearance and volume of distribution.

Clearance is the measure of the body's ability to eliminate a drug. As clearance decreases due, for example, to modifications to a drug, half-life would be expected to increase. However, this reciprocal relationship is exact only when there is no change in the volume of distribution. A useful approximate relationship between the terminal log-linear half-life ($t_{1/2}$), clearance (C), and volume of distribution (V) is given by the equation: $t_{1/2} \approx 0.693$ (V/C). Clearance does not indicate how much drug is being removed but, rather, the volume of biological fluid such as blood or plasma that would have to be completely freed of drug to account for the elimination. Clearance is expressed as a volume per unit of time (See Example 3).

The heterologous fusion proteins of the present invention comprise a FGF-21 compound fused to the Fc portion of an immunoglobulin, an analog of the Fc portion of an immunoglobulin, a fragment of the Fc portion of an immunoglobulin, human albumin, a human albumin analog, or a human albumin fragment. The C-terminus of the FGF-21 compound may be fused directly, or fused via a peptide linker, to the N-terminus of an albumin or Fc protein. Conversely, the N-terminus of the FGF-21 compound may be fused directly, or fused via a peptide linker, to the C-terminus of an albumin or Fc protein. These heterologous fusion proteins are biologically active and have an increased half-life compared to native FGF-21.

A "human FGF-21 mutein" is defined as comprising human FGF-21 in which at least one amino acid of the wild-type mature protein has been substituted by another amino acid. Examples of FGF-21 muteins are described in U.S. patent applications 60/528,582, 60/606,805, 60/606,830, and 60/635,882 herein incorporated by reference. Generally speaking, a mutein possesses some modified property, structural or functional, of the wild-type protein. For example, the mutein may have enhanced or improved physical stability in concentrated solutions (e.g., less hydrophobic mediated aggregation), while maintaining a favorable bioactivity profile. The mutein may possess increased compatibility with pharmaceutical preservatives (e.g., m-cresol, phenol, benzyl alcohol), thus enabling the preparation of a preserved pharmaceutical formulation that maintains the physiochemical properties and biological activity of the protein during storage. The mutein may have reduced O-glycosylation when expressed in yeast. The mutein may have less deamindation when compared to wild type FGF-21. As used herein, these terms are not limiting, it being entirely possible that a given mutein has one or more modified properties of the wild-type protein.

Examples of FGF-21 muteins with enhanced pharmaceutical stability include the substitution with a charged and/or polar but uncharged amino acid for one or more of the following: glycine 42, glutamine 54, arginine 77, alanine 81, leucine 86, phenylalanine 88, lysine 122, histidine 125, arginine 126, proline 130, arginine 131, leucine 139, alanine145, leucine 146, isoleucine 152, alanine 154, glutamine 156, glycine 161, serine 163, glycine 170, or serine 172 wherein the numbering of the amino acids is based on SEQ ID NO: 1. A charged amino acid is defined as a positively or negatively charged amino acid. A positively charged amino acid is defined to include histadine, lysine, arginine, and non-naturally occurring analogs thereof (e.g., gamma aminobutyric acid, ornithine, etc.). A negatively charged amino acid is defined to included aspartate, glutamate, and non-naturally occurring analogs thereof (e.g., aminoadipic acid). A polar but uncharged amino acid is defined to include serine, threonine, asparagine, glutamine, and non-naturally occurring analogs thereof. Preferred muteins are Gln54Glu, Leu139Glu, Ala145Glu, Leu146Glu, Ile152Glu, Gln156Glu, Ser163Glu, and Ile152Glu-Ser 163Glu.

Additional muteins of FGF-21 with enhanced pharmaceutical stability include FGF-21 with the substitution of a cysteine for two or more of the following: arginine 19, tyrosine 20, leucine 21, tyrosine 22, threonine 23, aspartate 24, aspartate 25, alanine 26, glutamine 27, lutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of the amino acids is based on SEQ ID NO:1.

Specific muteins of FGF-21 with engineered disulfide bonds, in addition to the naturally occurring one at Cys75-Cys93, are as follows: Gln76Cys-Ser109Cys, Cys75-Ser85Cys, Cys75-Ala92Cys, Phe73Cys-Cys93, Ser123Cys-His125-Cys, Asp102Cys -Tyr104Cys, Asp127Cys-Gly132Cys, Ser94Cys-Glu110Cys, Pro115Cys-His117Cys, Asn121Cys-Asp127Cys, Leu100Cys-Asp102Cys, Phe95Cys-Tyr107Cys, Arg19Cys-Pro 138Cys, Tyr20Cys-Leu139Cys, Tyr22Cys-Leu137Cys, Arg77Cys-Asp79Cys, Pro90Cys-Ala92Cys, Glu50Cys-Lys69Cys, Thr23Cys-Asp25Cys, Ala31Cys-Gly43Cys, Gln28Cys-Gly43Cys, Thr23Cys-Gln28Cys, Val141Cys-Leu82Cys, Leu58Cys-Val62Cys, Gln54Cys-Leu66Cys, Ile35Cys-Gly67Cys, Gly67Cys-Arg72Cys, Ile35Cys-Gly84Cys, Arg72Cys-Gly84Cys, or Arg77Cys-Ala81Cys, wherein the numbering of the amino acids is based on SEQ ID NO: 1. Preferred muteins with engineered disulfide bonds are Tyr22Cys-Leu139Cys; Asp24Cys-Arg135Cys; Leu118Cys-Gly132Cys; His117Cys-Pro 130Cys; His117Cys-Ala129Cys; Leu82Cys-Pro119Cys; Gly80Cys-Ala129Cys; Gly43Cys-Pro124Cys; Gly42Cys-Arg126Cys; Gly42Cys-Pro124Cys; Gln28Cys -Pro124Cys; Gln27Cys-Ser123Cys; Ala26Cys-Lys122Cys; or Asp25Cys-Lys122Cys. Most preferred muteins with engineered disulfide bonds are Leu118Cys-Ala134Cys; Leu21Cys-Leu33Cys; Ala26Cys-Lys122Cys; Leu21Cys-Leu33Cys/Leu118Cys-Ala 134Cys; Ile152Glu-Ser163Glu/Leu118Cys-Ala134Cys; and, Leu118Cys-Ala134Cys/Ser167Ala.

Examples of muteins of human FGF-21, or a biologically active peptide thereof, with reduced capacity of O-glycosylation when expressed in yeast compared to wild-type human FGF-21 include the substitution of any amino acid except Ser or Thr for Ser 167, in combination with the substitution of a cysteine for two or more of the following: arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of amino acids is based on SEQ ID NO:1. The most preferred muteins with reduced capacity of 0-glycosylation when expressed in yeast compared to wild-type human FGF-21 are Leu118Cys-Ala134Cys-Ser167Ala; Leu21Cys-Leu33Cys-Ser167Ala; Ala26Cys-Lys122Cys-Ser167Ala; or Leu21Cys -Leu33Cys/ Leu118Cys-Ala134Cys-Ser167Ala.

An FGF-21 compound also includes an "FGF-21 derivative" which is defined as a molecule having the amino acid sequence of FGF-21 or an FGF-21 analog, but additionally having a chemical modification of one or more of its amino acid side groups, α-carbon atoms, terminal amino group, or terminal carboxylic acid group. A chemical modification includes, but is not limited to, adding chemical moieties, creating new bonds, and removing chemical moieties.

Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist. The α-carbon of an amino acid may be mono- or dimethylated.

FGF-21 fusion proteins of the present invention have an in vitro biological activity that is comparable to that of native FGF-21. Although some FGF-21 fusion proteins of the invention may have biological activity lower than that of native FGF-21 as measured in a particular assay, this activity decrease is compensated by the compound's extended half-life and/or lower clearance value and may even be a favorable characteristic for an FGF-21 compound with an extended elimination half-life.

The FGF-21 fusion proteins of the present invention can comprise glycosylation sites. Glycosylation is a chemical modification wherein sugar moieties are added to the protein at specific sites. Glycosylation of proteins play a role in ensuring the correct charge, confirmation, and stability of maturing protein and can target the protein to the cell surface and eventual secretion of the protein. Most importantly, glycosylation effects the in vivo clearance rate for many proteins. Sugars can be O-linked or N-linked. Generally, O-linked sugars are added to the hydroxyl-group oxygen of serine and threonine, while N-linked sugars are added to the amide nitrogen of asparagine. The consensus site for N-glycosylation is Asn X1X2 wherein X1 is any amino acid except Pro and X2 is Ser or Thr.

Heterologaous Fc Fusion Proteins:

The FGF-21 compounds described above can be fused directly or via a peptide linker to the Fc portion of an immunoglobulin. Immunoglobulins are molecules containing polypeptide chains held together by disulfide bonds, typically having two light chains and two heavy chains. In each chain, one domain (V) has a variable amino acid sequence depending on the antibody specificity of the molecule. The other domains (C) have a rather constant sequence common to molecules of the same class.

As used herein, the Fc portion of an immunoglobulin has the meaning commonly given to the term in the field of immunology. Specifically, this term refers to an antibody fragment that is obtained by removing the two antigen binding regions (the Fab fragments) from the antibody. One way to remove the Fab fragments is to digest the immunoglobulin with papain protease. Thus, the Fc portion is formed from approximately equal sized fragments of the constant region from both heavy chains, which associate through non-covalent interactions and disulfide bonds. The Fc portion can include the hinge regions and extend through the CH2 and CH3 domains to the C-terminus of the antibody. Representative hinge regions for human and mouse immunoglobulins can be found in Antibody Engineering, A Practical Guide, Borrebaeck, C.A.K., ed., W.H. Freeman and Co., 1992, the teachings of which are herein incorporated by reference. The Fc portion can further include one or more glycosylation sites. The amino acid sequence of a representative Fc protein containing a hinge region, CH2 and CH3 domains, and one N-glycosylation site at position 82 is shown below:

[SEQ ID NO:3]
Ala Gln Pro Lys Ser Cys Asp Lys Thr His Thr Cys

Pro Pro Cys Pro Ala Pro Gln Lys Gly Gly Pro Ser

Val Phe Leu Phe Pro Pro Lys Pro Lys Asp Thr Lys

Met Ile Ser Arg Thr Pro Gln Val Thr Cys Val Val

Val Asp Val Ser His Glu Asp Pro Glu Val Lys Phe

-continued

```
Asn Trp Tyr Val Asp Gly Val Glu Val His Asn Ala

Lys Thr Lys Pro Arg Glu Glu Gln Tyr Asn Ser Thr

Tyr Arg Val Val Ser Val Leu Thr Val Leu His Gln

Asp Trp Leu Asn Gly Lys Glu Tyr Lys Cys Lys Val

Ser Asn Lys Ala Leu Pro Ala Pro Ile Glu Lys Thr

Ile Ser Lys Ala Lys Gly Gln Pro Arg Glu Pro Gln

Val Tyr Thr Leu Pro Pro Ser Arg Glu Glu Met Thr

Lys Asn Gln Val Ser Leu Thr Cys Leu Val Lys Gly

Phe Tyr Pro Ser Asp Ile Ala Val Glu Trp Glu Ser

Asn Gly Gln Pro Glu Asn Asn Tyr Lys Thr Thr Pro

Pro Val Leu Asp Ser Asp Gly Ser Phe Phe Leu Tyr

Ser Lys Leu Thr Val Asp Lys Ser Arg Trp Gln Gln

Gly Asn Val Phe Ser Cys Ser Val Met His Glu Ala

Leu His Asn His Tyr Thr Gln Lys Ser Leu Ser Leu

Ser Pro Gly Lys.
```

There are five types of human immunoglobulin Fc regions with different effector and pharmacokinetic properties: IgG, IgA, IgM, IgD, and IgE. IgG is the most abundant immunoglobulin in serum. IgG also has the longest half-life in serum of any immunoglobulin (23 days). Unlike other immunoglobulins, IgG is efficiently recirculated following binding to an Fc receptor. There are four IgG subclasses G1, G2, G3, and G4, each of which have different effect or functions. These effector functions are generally mediated through interaction with the Fc receptor (FcγR) or by binding C1q and fixing complement. Binding to FcγR can lead to antibody dependent cell mediated cytolysis, whereas binding to complement factors can lead to complement mediated cell lysis. In designing heterologous Fc fusion proteins wherein the Fc portion is being utilized solely for its ability to extend half-life, it is important to minimize any effector function. All IgG sub-classes are capable of binding to Fc receptors (CD16, CD32, CD64) with G1 and G3 being more effective than G2 and G4. The Fc receptor binding region of IgG is formed by residues located in both the hinge and the carboxy terminal regions of the CH2 domain.

Depending on the desired in vivo effect, the heterologous fusion proteins of the present invention may contain any of the isotypes described above or may contain mutated Fc regions wherein the complement and/or Fc receptor binding functions have been altered. Thus, the heterologous fusion proteins of the present invention may contain the entire Fc portion of an immunoglobulin, fragments of the Fc portion of an immunoglobulin, or analogs thereof fused to a FGF-21 compound.

The fusion proteins of the present invention can consist of single chain proteins or as multi-chain polypeptides. Two or more Fc fusion proteins can be produced such that they interact through disulfide bonds that naturally form between Fc regions. These multimers can be homogeneous with respect to the FGF-21 compound or they may contain different FGF-21 compounds fused at the N-terminus of the Fc portion of the fusion protein.

Regardless of the final structure of the fusion protein, the Fc or Fc-like region must serve to prolong the in vivo plasma half-life of the FGF-21 compound fused at the C-terminus or N-terminus. Furthermore, the fused FGF-21 compound must retain some biological activity. Biological activity can be determined by in vitro and in vivo methods known in the art. Representative biological assays are described in Examples 1 and 2.

It is preferable that the Fc region used for the heterologous fusion proteins of the present invention be derived from an IgG1 or an IgG4 Fc region. It is even more preferable that the heterologous fusion proteins of the present invention contain an Fc portion which is derived from human IgG4, but comprises one or more substitutions compared to the wild-type human sequence. As used herein, the Fc portion of an immunoglobulin has the meaning commonly given to the term in the field of immunology. Specifically, this term refers to an antibody fragment which does not contain the two antigen binding regions (the Fab fragments) from the antibody. The Fc portion consists of the constant region of an antibody from both heavy chains, which associate through non-covalent interactions and disulfide bonds. The Fc portion can include the hinge regions and extend through the CH2 and CH3 domains to the c-terminus of the antibody. The Fc portion can further include one or more glycosylation sites.

Thus, heterologous fusion proteins of the present invention are derived from the human IgG4 Fc region because of its reduced ability to bind FcγR and complement factors compared to other IgG sub-types. The human IgG4 Fc portion of an immunoglobulin fused to an FGF-21 compound of the present invention comprises the sequence of SEQ ID NO:4

(SEQ ID NO:4)
Ala-Glu-Ser-Lys-Tyr-Gly-Pro-Pro-Cys-Pro-$Xaa_{11}$-Cys-

Pro-Ala-Pro-$Xaa_{16}$-$Xaa_{17}$-$Xaa_{18}$-Gly-Gly-Pro-Ser-Val-

Phe-Leu-Phe-Pro-Pro-Lys-Pro-Lys-Asp-Thr-Leu-Met-

Ile-Ser-Arg-Thr-Pro-Glu-Val-Thr-Cys-Val-Val-Val-

Asp-Val-Ser-Gln-Glu-Asp-Pro-Glu-Val-Gln-Phe-Asn-

Trp-Tyr-Val-Asp-Gly-Val-Glu-Val-His-Asn-Ala-Lys-

Thr-Lys-Pro-Arg-Glu-Glu-Gln-Phe-$Xaa_{80}$-Ser-Thr-Tyr-

Arg-Val-Val-Ser-Val-Leu-Thr-Val-Leu-His-Gln-Asp-

Trp-Leu-Asn-Gly-Lys-Glu-Tyr-Lys-Cys-Lys-Val-Ser-

Asn-Lys-Gly-Leu-Pro-Ser-Ser-Ile-Glu-Lys-Thr-Ile-

Ser-Lys-Ala-Lys-Gly-Gln-Pro-Arg-Glu-Pro-Gln-Val-

Tyr-Thr-Leu-Pro-Pro-Ser-Gln-Glu-Glu-Met-Thr-Lys-

Asn-Gln-Val-Ser-Leu-Thr-Cys-Leu-Val-Lys-Gly-Phe-

Tyr-Pro-Ser-Asp-Ile-Ala-Val-Glu-Trp-Glu-Ser-Asn-

Gly-Gln-Pro-Glu-Asn-Asn-Tyr-Lys-Thr-Thr-Pro-Pro-

Val-Leu-Asp-Ser-Asp-Gly-Ser-Phe-Phe-Leu-Tyr-Ser-

Arg-Leu-Thr-Val-Asp-Lys-Ser-Arg-Trp-Gln-Glu-Gly-

Asn-Val-Phe-Ser-Cys-Ser-Val-Met-His-Glu-Ala-Leu-

His-Asn-His-Tyr-Thr-Gln-Lys-Ser-Leu-Ser-Leu-Ser-

Leu-Gly-$Xaa_{230}$ wherein:
Xaa at position 11 is Pro or Ser;
Xaa at position 16 is Pro or Glu;

Xaa at position 17 is Phe, Val, or Ala;
Xaa at position 18 is Leu, Glu, or Ala;
Xaa at position 80 is Asn or Ala; and
Xaa at position 230 is Lys or is absent.

Moreover, the IgG4 Fc region which is part of the heterologous fusion proteins of the present invention may contain one or more of the following substitutions that eliminate effector function: substitution of proline for serine at residue 228; substitution of proline for glutamate at residue 233; alanine or valine for phenylalanine at residue 234; and, alanine or glutamate for leucine at residue 235 (EU numbering, Kabat, E. A. et al. (1991) *Sequences of Proteins of Immunological Interest*, 5$^{th}$ Ed. U.S. Dept. of Health and Human Services, Bethesda, Md., NIH Publication no. 91-3242). These residues correspond to positions 11, 16, 17, and 18 in SEQ ID NO:4, respectively. Further, removing the N-linked glycosylation site in the IgG4 Fc region by substituting Ala for Asn at residue 297 (EU numbering) which corresponds to position 80 of SEQ ID NO:4 is another way to ensure that residual effector activity is eliminated in the context of a heterologous fusion protein.

The C-terminal lysine residue present in the native molecule may be deleted in the IgG4 derivative Fc portion of the heterologous fusion proteins discussed herein (position 230 of SEQ ID NO:4; deleted lysine referred to as des-K). Fusion proteins expressed in some cell types (such as NS0 cells) wherein lysine is encoded by the C-terminal codon are heterogeneous in that a portion of the molecules have lysine as the C-terminal amino acid and a portion have lysine deleted. The deletion is due to protease action during expression in some types of mammalian cells. Thus, to avoid this heterogeneity, it is preferred that Fc fusion expression constructs lack a C-terminal codon for lysine.

It is preferred that the C-terminal amino acid of the FGF-21 compound discussed herein is fused to the N-terminus of the IgG4 Fc analog portion via a glycine-rich linker (G-rich), designated by L, with the number immediately preceding the L referring to the number of linkers separating the FGF-21 compound from the Fc portion. The in vivo function and stability of the heterologous fusion proteins of the present invention can be optimized by adding the small peptide linkers to prevent potentially unwanted domain interactions. Further, a G-rich linker provides some structural flexibility such that the FGF-21 compound can interact productively with the receptor on target cells. These linkers, however, can significantly increase the risk that the fusion protein will be immunogenic in vivo. Thus, it is preferred that the length be no longer than necessary to prevent unwanted domain interactions and/or optimize biological activity and/or stability. Although more copies of this linker may be used in the heterologous fusion proteins of the present invention, it is preferred that a single copy of this linker be used to minimize the risk of immunogenicity associated with prolonged and repeated administration.

The FGF-21 compound and Fc or HSA portion of the heterologous fusion proteins of the present invention are preferably fused together via 1, 1.5 or 2 repeats of the G-rich peptide linker. The most preferred glycine-rich linker is designated 1L and comprises the sequence Gly-Gly-Gly-Gly-Ser-Gly-Gly-Gly-Gly-Ser-Gly-Gly-Gly-Gly-Ser (SEQ ID NO:5). Additional preferred peptide linkers include a linker specified as 1.5L, Gly-Ser -Gly-Gly-Gly-Gly-Ser-Gly-Gly-Gly-Gly-Ser-Gly-Gly-Gly-Gly-Ser-Gly-Gly-Gly-Gly-Ser (SEQ ID NO:6); a linker specified as 2L, Gly-Gly-Gly-Gly-Ser-Gly-Gly-Gly-Gly-Ser -Gly-Gly-Gly-Gly-Ser-Gly-Gly-Gly-Gly-Ser-Gly-Gly-Gly-Gly-Ser (SEQ ID NO:7); a linker specified as H1, Asp-Ala-Ala-Ala-Lys-Glu-Ala-Ala-Ala-Lys -Asp-Ala-Ala-Ala-Arg-Glu-Ala-Ala-Ala-Arg-Asp-Ala-Ala-Ala-Lys (SEQ ID NO:8); and, a linker specified as S1, Asn-Val-Asp-His-Lys-Pro-Ser-Asn-Thr-Lys-Val-Asp-Lys-Arg (SEQ ID NO:9). In some cases, 3, 4, 5, or even 6 repeats of the G-rich peptide linker may be utilized.

In the heterologous fusion proteins indicated below, IgG4 refers to an analog of the human IgG4 Fc sequence specified as SEQ ID NO:4. Substitutions in the IgG4 Fc portion of the heterologous fusion protein are indicated in parenthesis. The wild-type amino acid is specified by its common abbreviation followed by the position number in the context of the entire IgG4 sequence using the EU numbering system followed by the amino acid being substituted at that position specified by its common abbreviation.

Preferred FGF-21-Fc-heterlogous fusion proteins of the present invention include the following proteins: I152E/S163E/L118C/A134C-1L-IgG4 (S228P), I152E/S163E/L118C/A134C-1L-IgG4 (S228P, F234A, L235A), I152E/S163E/L118C/A134C-1L-IgG4 (S228P, N297A), I152E/S163E/L118C/A134C -1L-IgG4 (S228P, F234A, L235A, N297A), I152E/S163E/L118C/A134C-1.5L-IgG4 (S228P), I152E/S163E/L118C/A134C-1.5L-IgG4 (S228P, F234A, L235A), I152E/S163E/L118C/A134C-1.5L-IgG4 (S228P, N297A), I152E/S 163E/L118C/A134C -1.5L-IgG4 (S228P, F234A, L235A, N297A), I152E/S163E/L118C/A134C-2L -IgG4 (S228P), I152E/S163E/L118C/A134C-2L-IgG4 (S228P, F234A, L235A), I152E/S163E/L118C/A134C-2L-IgG4 (S228P, N297A), and I152E/S163E/L118C/A134C-2L-IgG4 (S228P, F234A, L235A, N297A).

More preferred FGF-21-Fc heterologous fusion proteins of the present invention include the following proteins: L118C/A134C-1L-IgG4 (S228P), L118C/A134C-1L -IgG4 (S228P, F234A, L235A), L118C/A134C-1L-IgG4 (S228P, N297A), L118C/A134C-1L-IgG4 (S228P, F234A, L235A, N297A), L118C/A134C-1.5L-IgG4 (S228P), L118C/Ai34C-1.5L-IgG4 (S228P, F234A, L235A), L118C/A134C-1.5L-IgG4 (S228P, N297A), L118C/A134C-1.5L-IgG4 (S228P, F234A, L235A, N297A), L118C/A134C-2L-IgG4 (S228P), L118C/A134C-2L-IgG4 (S228P, F234A, L235A), L118C/A134C-2L-IgG4 (S228P, N297A), and L118C/A134C-2L-IgG4 (S228P, F234A, L235A, N297A).

Even more preferred FGF-21-Fc heterologous fusion proteins of the present invention include the following proteins: L118C/A134C/S167A-1L-IgG4 (S228P); L118C/A134C/S167A -1L-IgG4 (S228P, F234A, L235A), L118C/A134C/S167A-1L-IgG4 (S228P, N297A), L118C/A134C/S167A-1L-IgG4 (S228P, F234A, L235A, N297A), L118C/A134C/S167A-1.5L-IgG4 (S228P), L118C/A134C/S167A-1.5L-IgG4 (S228P, F234A, L235A), L118C/A134C/S167A-1.5L-IgG4 (S228P, N297A), L118C/A134C/S167A-1.5L-IgG4 (S228P, F234A, L235A, N297A), L118C/A134C/S 167A-2L-IgG4 (S228P), L118C/A134C/S167A-2L-IgG4 (S228P, N297A), F234A, L235A), L118C/A134C/S167A-2L-IgG4 (S228P, N297A), and L118C/A134C/S167A-2L-IgG4 (S228P, F234A, L235A, N297A).

Heterolous Albumin Fusion Proteins:

The FGF-21 compounds described above can be fused directly or via a peptide linker to albumin or an analog, fragment, or derivative thereof.

Generally the albumin proteins making up part of the fusion proteins of the present invention can be derived from albumin cloned from any species. However, human albumin and fragments and analogs thereof are preferred to reduce the risk of the fusion protein being immunogenic in humans. Human serum albumin (HSA) consists of a single non-glycosylated polypeptide chain of 585 amino acids with a formula molecular weight of 66,500. The amino acid sequence of human HSA is:

[SEQ ID NO:10]

```
Asp Ala His Lys Ser Glu Val Ala His Arg Phe Lys
Asp Leu Gly Glu Glu Asn Phe Lys Ala Leu Val Leu
Ile Ala Phe Ala Gln Tyr Leu Gln Gln Cys Pro Phe
Glu Asp His Val Lys Leu Val Asn Glu Val Thr Glu
Phe Ala Lys Thr Cys Val Ala Asp Glu Ser Ala Glu
Asn Cys Asp Lys Ser Leu His Thr Leu Phe Gly Asp
Lys Leu Cys Thr Val Ala Thr Leu Arg Glu Thr Tyr
Gly Glu Met Ala Asp Cys Cys Ala Lys Gln Glu Pro
Glu Arg Asn Glu Cys Phe Leu Gln His Lys Asp Asp
Asn Pro Asn Leu Pro Arg Leu Val Arg Pro Glu Val
Asp Val Met Cys Thr Ala Phe His Asp Asn Glu Glu
Thr Phe Leu Lys Lys Tyr Leu Tyr Glu Ile Ala Arg
Arg His Pro Tyr Phe Tyr Ala Pro Glu Leu Leu Phe
Phe Ala Lys Arg Tyr Lys Ala Ala Phe Thr Glu Cys
Cys Gln Ala Ala Asp Lys Ala Ala Cys Leu Leu Pro
Lys Leu Asp Glu Leu Arg Asp Glu Gly Lys Ala Ser
Ser Ala Lys Gln Arg Leu Lys Cys Ala Ser Leu Gln
Lys Phe Gly Glu Arg Ala Phe Lys Ala Trp Ala Val
Ala Arg Leu Ser Gln Arg Phe Pro Lys Ala Glu Phe
Ala Glu Val Ser Lys Leu Val Thr Asp Leu Thr Lys
Val His Thr Glu Cys Cys His Gly Asp Leu Leu Glu
Cys Ala Asp Asp Arg Ala Asp Leu Ala Lys Tyr Ile
Cys Glu Asn Gln Asp Ser Ile Ser Ser Lys Leu Lys
Glu Cys Cys Glu Lys Pro Leu Leu Glu Lys Ser His
Cys Ile Ala Glu Val Glu Asn Asp Glu Met Pro Ala
Asp Leu Pro Ser Leu Ala Ala Asp Phe Val Glu Ser
Lys Asp Val Cys Lys Asn Tyr Ala Glu Ala Lys Asp
Val Phe Leu Gly Met Phe Leu Tyr Glu Tyr Ala Arg
Arg His Pro Asp Tyr Ser Val Val Leu Leu Leu Arg
Leu Ala Lys Thr Tyr Glu Thr Thr Leu Glu Lys Cys
Cyc Ala Ala Ala Asp Pro His Glu Cys Tyr Ala Lys
Val Phe Asp Glu Phe Lys Pro Leu Val Glu Glu Pro
Gln Asn Leu Ile Lys Gln Asn Cys Glu Leu Phe Glu
Asn Leu Gly Glu Tyr Lys Phe Gln Asn Ala Leu Leu
Val Arg Tyr Thr Lys Lys Val Pro Gln Val Ser Thr
Pro Thr Leu Val Glu Val Ser Arg Asn Leu Gly Lys
Val Gly Ser Lys Cys Cys Lys His Pro Glu Ala Lys
Arg Met Pro Cys Ala Glu Asp Tyr Leu Ser Val Val
Leu Asn Gln Leu Cys Val Leu His Glu Lys Thr Pro
Val Ser Asp Arg Val Thr Lys Cys Cys Thr Glu Ser
Leu Val Asn Arg Arg Pro Cys Phe Ser Ala Leu Glu
Val Asp Glu Thr Tyr Val Pro Lys Glu Phe Asn Ala
Glu Thr Phe Thr Phe His Ala Asp Ile Cys Thr Leu
Ser Glu Lys Glu Arg Gln Ile Lys Lys Gln Thr Ala
Leu Val Glu Leu Val Lys His Lys Pro Lys Ala Thr
Lys Glu Gln Leu Lys Ala Val Met Asp Asp Phe Ala
Ala Phe Val Glu Lys Cys Cys Lys Ala Asp Asp Lys
Glu Thr Cys Phe Ala Glu Glu Gly Lys Lys Leu Val
Ala Ala Ser Gln Ala Ala Leu Gly Leu.
```

[See Meloun, et al. (1975) FEBS Letters 58:136; Behrens, et al. (1975) Fed. Proc. 34:591; Lawn, et al. (1981) Nucleic Acids Research 9:6102-6114; Minghetti, et al. (1986) J. Biol. Chem. 261:6747]. A variety of polymorphic variants as well as analogs and fragments of albumin have been described. [See Weitkamp, et al., (1973) Ann. Hum. Genet. 37:219]. For example, in EP 322,094, the inventors disclose various shorter forms of HSA. Some of these fragments include HSA (1-373), HSA(1-388), HSA(1-389), HSA(1-369), and HSA (1-419) and fragments between 1-369 and 1-419. EP 399,666 discloses albumin fragments that include HSA(1-177) and HSA(1-200) and fragments between HSA(1-177) and HSA (1-200).

It is understood that the heterologous fusion proteins of the present invention include FGF-21 compounds that are coupled to any albumin protein including fragments, analogs, and derivatives wherein such fusion protein is biologically active and has a longer plasma half-life than the FGF-21 compound alone. Thus, the albumin portion of the fusion protein need not necessarily have a plasma half-life equal to that of native human albumin. Fragments, analogs, and derivatives are known or can be generated that have longer half-lives or have half-lives intermediate to that of native human albumin and the FGF-21 compound of interest.

The heterologous fusion proteins of the present invention encompass proteins having conservative amino acid substitutions in the FGF-21 compound and/or the Fc or albumin portion of the fusion protein. A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Except as otherwise specifically provided herein, conservative substitutions are preferably made with naturally occurring amino acids.

As outlined above, amino acid substitutions in the fusion proteins of the present invention can be based on the relative similarity of the amino acid side-chain substituents, for example, their hydrophobicity, hydrophilicity, charge, size, etc. Furthermore, substitutions can be made based on secondary structure propensity. For example, a helical amino acid can be replaced with an amino acid that would preserve the helical structure. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids.

The FGF-21 compounds of the present invention may be generated and/or isolated by any means known in the art. Because of the size of the fusion proteins, recombinant methods are preferred such as described in Sambrook et al., *Molecular Cloning: A Laboratory Manual*, Cold Spring Harbor Laboratory Press, NY (1989).

Various methods of protein purification may be employed and such methods are known in the art and described, for example, in Deutscher, *Methods in Enzymology* 182: 83-9 (1990) and Scopes, *Protein Purification: Principles and Practice*, Springer-Verlag, NY (1982). The purification step(s) selected will depend, for example, on the nature of the production process used for FGF-21

Wild-type human IgG4 proteins can be obtained from a variety of sources. For example, these proteins can be obtained from a cDNA library prepared from cells that express the mRNA of interest at a detectable level. Libraries can be screened with probes designed using the published DNA or protein sequence for the particular protein of interest. For example, immunoglobulin light or heavy chain constant regions are described in Adams, et al. (1980) Biochemistry 19:2711-2719; Goughet, et al. (1980) Biochemistry 19:2702-2710; Dolby, et al. (1980) Proc. Natl. Acad. Sci. USA 77:6027-6031; Rice et al. (1982) Proc. Natl. Acad. Sci. USA 79:7862-7862; Falkner, et al. (1982) Nature 298:286-288; and Morrison, et al. (1984) Ann. Rev. Immunol. 2:239-256.

Screening a cDNA or genomic library with the selected probe may be conducted using standard procedures, such as described in Sambrook et al., *Molecular Cloning: A Laboratory Manual*, Cold Spring Harbor Laboratory Press, NY (1989). An alternative means to isolate a gene encoding an immunoglobulin protein is to use PCR methodology [Sambrook et al., supra; Dieffenbach et al., *PCR Printer: A Laboratory Manual*, Cold Spring Harbor Laboratory Press, NY (1995)]. PCR primers can be designed based on published sequences.

Generally the full-length wild-type sequences cloned from a particular library can serve as a template to create the IgG4 Fc analog fragments of the present invention that retain the ability to confer a longer plasma half-life on the FGF-21 compound that is part of the fusion protein. The IgG4 Fc analog fragments can be generated using PCR techniques with primers designed to hybridize to sequences corresponding to the desired ends of the fragment. PCR primers can also be designed to create restriction enzyme sites to facilitate cloning into expression vectors.

The gene encoding a fusion protein can then be constructed by ligating DNA encoding a FGF-21 compound in-frame to DNA encoding the IgG Fc proteins described herein. The DNA encoding the FGF-21 compound and IgG4 Fc fragments can be mutated either before ligation or in the context of a cDNA encoding an entire fusion protein. A variety of mutagenesis techniques are well known in the art. The gene encoding the FGF-21 compound and the gene encoding the IgG4 Fc analog protein can also be joined in-frame via DNA encoding a G-rich linker peptide.

FGF-21 compounds have a variety of biological activities. FGF-21 is particularly promising as a treatment for non-insulin dependent diabetes mellitus (NIDDM, type 2) as it does not present a risk of hypoglycemia as do present NIDDM treatments. FGF-21 is also contemplated to be a treatment for obesity and metabolic syndrome.

It is also considered that a use of FGF-21 fusion proteins of the present invention includes use in the manufacture of a medicament for the treatment of type 2 diabetes, obesity and metabolic syndrome. FGF-21 fusion proteins may be combined with other modifications known in the art to increase FGF-21 half-life and thereby increase the half-life of the compound even further than a fusion protein alone or the other modification method alone.

As used herein, the term "FGF-21 compound" also includes pharmaceutically acceptable salts of the compounds described herein. An FGF-21 compound of this invention can possess a sufficiently acidic, a sufficiently basic, or both functional groups, and accordingly react with any of a number of inorganic bases, and inorganic and organic acids, to form a salt.

The FGF-21 fusion proteins of the present invention are particularly suited for parenteral administration, they can be also be delivered orally, by nasal administration, or by inhalation. Parenteral administration can include, for example, systemic administration, such as by intramuscular, intravenous, subcutaneous, or intraperitoneal injection. The FGF-21 fusion proteins can be administered to the subject in conjunction with an acceptable pharmaceutical carrier, diluent or excipient as part of a pharmaceutical composition for treating the diseases discussed above. The pharmaceutical composition can be a solution or, if administered parenterally, a suspension of the FGF-21. Suitable pharmaceutical carriers may contain inert ingredients which do not interact with the peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Some examples of suitable excipients include lactose, dextrose, sucrose, trehalose, sorbitol, and mannitol.

The FGF-21 fusion proteins of the invention may be formulated for administration such that blood plasma levels are maintained in the efficacious range for extended time periods.

A "therapeutically effective amount" of a FGF-21 fusion protein is the quantity that results in a desired therapeutic and/or prophylactic effect without causing unacceptable side-effects when administered to a subject. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a FGF-21 fusion protein for the treatment of type 2 diabetes is the quantity that would result in greater control of blood glucose concentration than in the absence of treatment, thereby resulting in a delay in the onset of diabetic complications such as retinopathy, neuropathy or kidney disease. An "effective amount" of a FGF-21 fusion protein for the prevention of diabetes is the quantity that would delay, compared with the absence of treatment, the onset of elevated blood glucose levels that require treatment with anti-hypoglycaemic drugs such as sulfonyl ureas, thiazolidinediones, insulin and/or bisguanidines. Moreover, a "therapeutically effective amount" of the FGF-21 fusion protein administered to a subject will also depend on the type and severity of the disease and on the characteristics of the subject, such as general health, age, sex, body weight and tolerance to drugs.

Those skilled in the art can readily optimize pharmaceutically effective dosages and administration regimens for therapeutic compositions comprising a FGF-21 fusion protein, as determined by good medical practice and the clinical condition of the individual patient. A typical dose range for the FGF-21 fusion proteins of the present invention will range from about 0.01 mg/kg to about 1000 mg/kg body weight. Preferably, the dosage ranges from about 0.1 mg/kg to about 100 mg/kg, more preferably from about 1.0 mg/kg to about 10 mg/kg. Most preferably, the dosage is about 1-5 mg/kg body weight. The appropriate dose of a FGF-21 fusion protein administered will result in lowering blood glucose levels and increasing energy expenditure by faster and more efficient glucose utilization, and thus is useful for treating type 2 diabetes, obesity and metabolic syndrome. The frequency of dosing is determined by the plasma half life/clearance of the FGF-21 fusion protein. Preferably, dosing will be about every 2 days. More preferably, dosing will be about twice weekly. Even more preferably, dosing will be about once weekly. Most preferably, dosing will be about twice a month.

Having now described the present invention in detail, the same will be more clearly understood by reference to the following examples, which are included herewith for purposes of illustration only and are not intended to be limiting of the invention.

All patents and publications referred to herein are expressly incorporated by reference.

PREPARATION 1

Expression and Purification a FGF-21 Fusion Protein in HEK293EBNA Cells

Alternatively, FGF-21 fusion proteins are produced in a mammalian cell expression system using HEK293EBNA cells (EdgeBiosystems, Gaiethersburg, Md.). FGF-21 fusion proteins are subcloned in the proprietary expression vector representing a modification of commercially available pEAK10, between NheI and XbaI restriction sites in the MCS. The cDNA sequence encoding an FGF-21 fusion protein is fused in frame with the Igκ leader sequence to enhance secretion of the desired product in the tissue culture media. The expression is driven by the strong viral CMV promoter. HEK293EBNA cells are transiently transfected using a standard transfection reagent such as Fugene (Roche Diagnostics, Indianapolis Ind., USA) and the appropriate amount of recombinant plasmid, either as a monolayer or suspension culture, at the adequate cell density. Cells are incubated at 37° C. and 5% $CO_2$, in serum free media, and collections are made every day for 5 days. Typically the expression level in the HEK293EBNA suspension culture is ~30 mg/L. The expression of an FGF-21 fusion protein in mammalian cells yields the natural N-terminal sequence, HPIP, i.e. without a methionine residue at the N-terminus To purify a FGF-21 Fc fusion protein from HEK293EBNA cells, concentrated cell culture supernatant is loaded onto a 5 ml HiTrap rProtein A FF column (Amersham Biosciences AB, Uppsala, Sweden) equilibrated in PBS, pH 7.4, and proteins are eluted with 50 mM citric acid, pH3.3. The fractions are immediately neutralized with Tris and 0.5 M NaOH. The fraction pool is concentrated with Millipore 30K Amicon ultra centrifugal filter devices (UFC903024) and loaded onto a 26/60 Superdex 200 column (Amersham Bioscience AB, Uppsala, Sweden) equilibrated in PBS, pH7.4. Fractions are analyzed by SDS PAGE, pooled and concentrated by Millipore 30K Amicon ultra centrifugal filter devices and filter sterilized using a 0.22 μm MILLEX-GV filter (Millipore SLGVR25CS). The final concentration is determined by absorbance at 280 nm (scatter corrected). MALDI and N-terminal sequence are used to confirm the protein.

To purify an FGF-21 HSA fusion protein from HEK293EBNA cells, concentrated cell culture supernatant is loaded onto a self-packed 20 ml FF Q Sepharose column equilibrated in 20 mM Tris, pH7.5. Protein is eluted using a linear gradient from 0 to 500 mM NaCl, appropriate fractions are pooled, acetonitile with 0.1% TFA is added to a final concentration of 20%, and the material is loaded onto a Vydac protein C4 10×250 mm column, (Cat# 214TP510) equilibrated with 0.1% TFA in water. Protein is eluted using a linear gradient from 20 to 50% acetonitrile. The fraction pool is concentrated with Millipore 30K Amicon ultra centrifugal filter devices (UFC903024) and loaded onto a 26/60 Superdex 200 column (Amersham Bioscience AB, Uppsala, Sweden), equilibrated in PBS, pH7.4. Fractions are analyzed by SDS-PAGE, pooled, concentrated and filter sterilized. The final concentration is determined by absorbance at 280 nm (scatter corrected). MALDI and N-terminal sequence are used to confirm the protein.

Preparation 2

Expression of a FGF-21 fusion protein in Yeast

Yet another expression system for production of a FGF-21 fusion protein is yeast, such as *Pichia pastoris*, *Pichia methanolica* or *Saccharomyces cerevisiae*. For production in *Pichia pastoris*, a commercially available system (Invitrogen, Carlsbad, Calif.) uses vectors with the powerful AOX1 (alcohol oxidase) promters to drive high-level expression of recombinant proteins. Alternatively, vectors that use the promoter from the GAP gene (glyceraldehyde-3-phosphate dehydrogenase) are available for high level constitutive expression. The multi-copy *Pichia* expression vectors allow one to obtain strains with multiple copies of the gene of interest integrated into the genome. Increasing the number of copies of the gene of interest in a recombinant *Pichia* strain can increase protein expression levels.

EXAMPLE 1

Glucose Uptake in Mouse 3T3-L1 Adipocytes

3T3-L1 cells are obtained from the American Type Culture Collection (ATCC, Rockville, Md.). Cells are cultured in growth medium (GM) containing 10% iron-enriched fetal bovine serum in Dulbecco's modified Eagle's medium. For standard adipocyte differentiation, two days after cells reached confluency (referred as day 0), cells are exposed to differentiation medium (DM) containing 10% fetal bovine serum, 10 μg/ml of insulin, 1 μM dexamethasone, and 0.5 μM isobutylmethylxanthine, for 48 h. Cells then are maintained in post differentiation medium containing 10% fetal bovine serum, and 10 μg/ml of insulin.

Glucose Transport Assay—Hexose uptake, as assayed by the accumulation of 0.1 mM 2-deoxy-D-[$^{14}$C]glucose, is measured as follows: 3T3-L1 adipocytes in 12-well plates are washed twice with KRP buffer (136 mM NaCl, 4.7 mM KCl, 10 mM $NaPO_4$, 0.9 mM $CaCl_2$, 0.9 mM $MgSO_4$, pH 7.4)

warmed to 37° C. and containing 0.2% BSA, incubated in Leibovitz's L-15 medium containing 0.2% BSA for 2 h at 37° C. in room air, washed twice again with KRP containing, 0.2% BSA buffer, and incubated in KRP, 0.2% BSA buffer in the absence (Me$_2$SO only) or presence of wortmannin for 30 min at 37° C. in room air. Insulin is then added to a final concentration of 100 nM for 15 min, and the uptake of 2-deoxy-D-[$^{14}$C]glucose is measured for the last 4 min. Non-specific uptake, measured in the presence of 10 μM cytochalasin B, is subtracted from all values. Protein concentrations are determined with the Pierce bicinchoninic acid assay. Uptake is measured routinely in triplicate or quadruplicate for each experiment.

In vitro potency (EC$_{50}$) is compared to the in vitro activity of wild-type FGF-21. The in vitro potency of FGF-21 fusion proteins of the present invention is compared to wild-type FGF-21 in Table 1. As indicated in Table 1, the FGF-21 fusion proteins of the present invention have reduced in vitro potency to various degrees compare to wild-type FGF-21. However, the decrease in in vitro potency is likely compensated for with the increase in time extension (plasma half life) of the FGF-21 fusion protein.

TABLE 1

| FGF-21 Fusion Protein | In vitro Potency EC$_{50}$ (nM) |
| --- | --- |
| Wild-type Control | 1.1 |
| FGF-21-Fc* | 13.3 |
| FGF-21-L-Fc** | 124 |
| FGF-21-L-IgG4m-e** | 89 |
| FGF-21-L-HSA** | 73 |
| HSA-L-FGF-21*** | 2.2 |
| Fc-L-FGF-21*** | 7.2 |

*C-terminus of FGF-21 fused to the N-terminus of the fusion protein
**C-terminus of FGF-21 fused to the N-terminus of the fusion protein via a linker peptide, (Gly-Gly-Gly-GLy-Ser)$_3$.
***N-terminus of FGF-21 fused to the C-terminus of the fusion protein via a linker peptide, (Gly-Gly-Gly-GLy-Ser)$_3$.

Example 2

In Vivo Analysis of FGF-21-Fc Fusion Proteins in the Ob/ob Mouse Model

The Ob/ob mouse model is an animal model for hyperglycemia, insulin resistance and obesity. Male ob/ob mice are used to monitor plasma glucose levels and triglyceride levels after treatment with FGF-21 fusion proteins compared to FGF-21 alone. The test groups of male ob/ob mice (7 weeks old) are: (1) s.c. vehicle control (0.9% NaCl, 0.1 ml/mouse) for seven days; (2) FGF-21, 11 μg/day, administered by continuous infusion for seven days (Alzet pumps 1007D, 100 mcl, 0.5 mcl/h); (3) FGF-21-Fc fusion protein, 2.55 nM, administered on Day 0 only; (4) FGF-21-Fc fusion protein, 1.5 nM, administered on Day 0 only.; (5) FGF-21-Fc fusion protein, 0.5 nM, administered on Day 0 only. FGF-21-Fc fusion protein is administered s.c. in 0.1 ml.

Blood glucose levels are measured daily for 7 days, 1 hour post dosing, using a standard protocol. The extended time action of FGF-21-Fc fusion proteins is indicated in Table 2 where a single dose on day 0 lowers blood glucose levels for 6 days.

TABLE 2

Blood Glucose Levels in ob/ob mice (mg/dl)
Days of Treatment

| Treatment | 0 | 1 | 2 | 3 | 4 | 5 | 6 | 7 |
| --- | --- | --- | --- | --- | --- | --- | --- | --- |
| Veh. Ctl. (s.c.) | 280 | 288 | 295 | 253 | 260 | 254 | 296 | 321 |
| FGF-21 11 μg/day for 7 days | 281 | 237 | 168 | 154 | 135 | 129 | 124 | 157 |
| FGF-21-Fc* 2.55 nM, day 0 only | 281 | 225 | 181 | 177 | 166 | 198 | 195 | 273 |
| FGF-21-Fc* 1.5 nM, day 0 only | 279 | 253 | 221 | 226 | 205 | 246 | 241 | 328 |
| FGF-21-Fc* 0.5 nM, day 0 only | 279 | 232 | 218 | 216 | 234 | 252 | 220 | 304 |

*FGF-21-Fc fusion proteins: FGF-21 C terminus is fused to the N-terminus of an IgG4 Fc, without a linker peptide.

In another experiment, male ob/ob mice are used to monitor plasma glucose levels after a single treatment with a FGF-21 fusion protein fused with a linker peptide, compared to continuous infusion of FGF-21 alone. The test groups of male ob/ob mice (7 weeks old) are: (1) vehicle control (0.9% NaCl) by continuous infusion for seven days (Alzet pumps 1007D, 100 mcl, 0.5 mcl/h); (2) FGF-21, 3.4 nM by continuous infusion for seven days; (3) FGF-21-L-Fc fusion protein, 3.4 nM; administered s.c. in 0.1 ml on Day 0 only; and (4) Fc-L-FGF-21 fusion protein, 3.4 nM administered s.c. in 0.1 ml on Day 0 only; (5) FGF-21-L-HSA fusion protein, 3.4 nM administered s.c. in 0.1 ml on Day 0 only. L is the peptide linker, (Gly-Gly-Gly-Gly-Ser)$_3$, in the above fusion proteins The animals of groups (1) and (2) are dosed by continuous infusion for 7 days and groups (3) through (5) are dosed on day 0 only. Blood glucose levels are measured daily for 7 days, 1 hour post dosing, using a standard protocol. The superior extended time action of FGF-21 fusion proteins is demonstrated in Table 3, where a single dose on day 0 lowers blood glucose levels for 7 days.

In addition, plasma triglyceride levels are measured on day 7 of the experiment. The superior extended time action of FGF-21 fusion proteins is demonstrated in Table 4 where a single dose on day 0 lowers plasma triglyceride levels for 7 days.

TABLE 3

Blood Glucose Levels in ob/ob mice (mg/dl)*
Days of Treatment

| Treatment | 0 | 1 | 2 | 3 | 4 | 5 | 6 | 7 |
| --- | --- | --- | --- | --- | --- | --- | --- | --- |
| Veh. Ctl. Continuous infusion | 280 | 270 | 215 | 200 | 200 | 230 | 250 | 310 |
| FGF-21 3.4 nM Continuous infusion | 281 | 230 | 175 | 130 | 135 | 140 | 130 | 155 |
| FGF-21-L-Fc* 3.4 nM, | 279 | 210 | 180 | 140 | 135 | 140 | 150 | 200 |
| Fc-L-FGF-21** 1.5 nM, | 279 | 240 | 225 | 165 | 167 | 205 | 230 | 228 |

TABLE 3-continued

| Treatment | Blood Glucose Levels in ob/ob mice (mg/dl)* Days of Treatment | | | | | | | |
|---|---|---|---|---|---|---|---|---|
| | 0 | 1 | 2 | 3 | 4 | 5 | 6 | 7 |
| FGF-21-L-HSA[+] 2.55 nM, | 281 | 235 | 170 | 130 | 155 | 185 | 215 | 250 |

*FGF-21 C terminus fused to the N-terminus of an IgG4 Fc
**C-terminus of an IgG4 Fc fused to the N terminus of FGF-21
[+]FGF-21 C terminus fused to the N-terminus of HSA

TABLE 4

| Test Group | Day 7 Plasma Triglycerides (mmol/l) |
|---|---|
| Vehicle control | 640 |
| FGF-21 Control, 3.4 nM | 280 |
| FGF-21-L-Fc* | 400 |
| Fc-L-FGF-21** | 490 |
| FGF-21-L-HSA* | 380 |

*C-terminus of FGF-21 fused to the N-terminus of the fusion protein via a linker peptide, (Gly-Gly-Gly-Gly-Ser)$_3$.
**N-terminus of FGF-21 fused to the C-terminus of the fusion protein via a linker peptide, (Gly-Gly-Gly-Gly-Ser)$_3$.

Example 3

Pharmacokinetic Analysis of FGF-21 Fusion Proteins

FGF-21 fusion proteins are administered by intravenous (IV) or subcutaneous (SC) routes at a dose of 0.4 mg/kg to CD-1 mice. The animals are bled at various times between 0 and 336 hours after dosing. Plasma is collected from each sample and analyzed by radioimmunoassay. Pharmacokinetic parameters are calculated using model-dependent (IV data) and independent (SC data) methods (WinNonlin Pro) and are reported in Table 5 below. By IV administration, the FGF-21-Fc fusion protein has an elimination half-life of approximately 53.9 hours compared to an elimination half-life of 0.5 hours for native FGF-21. By SC administration the FGF-21-Fc fusion protein has an elimination half-life of approximately 24 hours compared to an elimination half-life of 0.6 hours for native FGF-21. By both routes of administration the FGF-21-Fc fusion protein demonstrates prolonged time action when compared to native FGF-21.

By IV administration, the FGF-21-HSA fusion protein has an elimination half-life of approximately 14.3 hours compared to an elimination half-life of 0.5 hours for native FGF-21. By SC administration the FGF-21-HSA fusion protein has an elimination half-life of approximately 8 hours compared to an elimination half-life of 0.6 hours for native FGF-21. By both routes of administration the FGF-21-HSA fusion protein demonstrates prolonged time action when compared to native FGF-21.

TABLE 5

| Compound | Route | $C_{max}$[a] (ng/mL) | $T_{max}$[b] (d) | $AUC_{0-\infty}$[c] (ng * h/mL) | $t_{1/2}$[d] (h) | CL/F[e] (mL/ h/kg) | %F[g] |
|---|---|---|---|---|---|---|---|
| FGF-21- | IV | 4432 | — | 137383 | 53.9 | 2.9 | 10 |
| Fc | SC | 1899 | 24 | 145056 | 48.6 | 2.8 | 6 |
| FGF-21- | IV | 6577 | — | 69886 | 14.3 | 5.7 | −53 |
| HSA | SC | 1380 | 8 | 37098 | 14.5 | 10.8 | |
| FGF-21 | IV | 4300 | — | 1200 | 0.5 | 803 | — |
| | SC | 440 | 1.0 | 980 | 0.6 | 1024 | 78 |

[a]Maximum observed plasma concentration.
[b]Time of maximum observed plasma concentration.
[c]Area under the plasma concentration-time curve measured from 0 to infinity.
[d]Elimination half-life in hours.
[e]Total body clearance as a function of bioavailability.
[g]Percent bioavailability.

We claim:

1. A heterologous fusion protein comprising a first polypeptide fused to a second polypeptide wherein the C-terminus of the first polypeptide is fused to the N-terminus of the second polypeptide via a linker and wherein the first polypeptide is a human FGF-21 mutein selected from the group consisting of:
   (a) SEQ ID NO:1 having mutations Leu118Cys-Ala134Cys;
   (b) SEQ ID NO:1 having mutations Leu21Cys-Leu33Cys;
   (c) SEQ ID NO:1 having mutations Ala26Cys-Lys122Cys;
   (d) SEQ ID NO:1 having mutations Ala31Cys-Gly43Cys;
   (e) SEQ ID NO:1 having mutations Leu21Cys-Leu33Cys/Leu118Cys-Ala134Cys;
   (f) SEQ ID NO:1 having mutations Ile52Glu-Ser163Glu/Leu118Cys-Ala134Cys; and
   (g) SEQ ID NO:1 having mutations Leu118Cys-Ala134Cys/Ser167Ala;
   wherein the second polypeptide is selected from the group consisting of:
   (a) the Fc portion of an immunoglobulin;
   (b) fragments of the Fc portion of an immunoglobulin;
   (c) human albumin; and
   (d) fragments of human albumin;
   and wherein the linker is selected from the group consisting of SEQ ID NO:5, SEQ ID NO:6, SEQ ID NO:7, SEQ ID NO:8, SEQ ID NO:9, [SEQ ID NO: 5]$_3$, [SEQ ID NO: 5]$_4$, [SEQ ID NO:5]$_5$, and [SEQ ID NO: 5]$_6$.

2. A heterologous fusion protein comprising a first polypeptide fused to a second polypeptide wherein the N-terminus of the first polypeptide is fused to the C-terminus of the second polypeptide via a linker and wherein the first polypeptide is selected from the group consisting of:
   (a) the Fc portion of an immunoglobulin;
   (b) fragments of the Fc portion of an immunoglobulin;
   (c) human albumin; and
   (d) fragments of human albumin;
   wherein the second polypeptide is a human FGF-21 mutein selected from the group consisting of:
   (a) SEQ ID NO:1 having mutations Leu 118Cys-Ala134Cys;
   (b) SEQ ID NO:1 having mutations Leu21Cys-Leu33Cys;
   (c) SEQ ID NO:1 having mutations Ala26Cys-Lys122Cys;
   (d) SEQ ID NO:1 having mutations Ala31Cys-Gly43Cys;
   (e) SEQ ID NO:1 having mutations Leu21Cys-Leu33Cys/Leu118Cys-Ala134Cys;
   (f) SEQ ID NO:1 having mutations Ile52Glu-Ser163Glu/Leu118Cys-Ala134Cys; and (g) SEQ ID NO:1 having mutations Leu 118Cys-Ala134Cys/Ser167Ala;

and, wherein the linker is selected from the group consisting of SEQ ID NO:5, SEQ ID NO:6, SEQ ID NO:7, SEQ ID NO:8, SEQ ID NO:9, [SEQ ID NO: 5]$_3$, [SEQ ID NO: 5]$_4$, [SEQ ID NO:5]$_5$, and [SEQ ID NO: 5]$_6$.

3. A heterologous human FGF-21/human IgG4 Fc region fusion protein selected from the group consisting of:

(a) SEQ ID NO:1 having mutations Leu 118Cys/Ala134Cys/Ser167Ala fused to SEQ ID NO:5 fused to SEQ ID NO: 4 having mutation Ser11Pro, fused in the N-terminal to C-terminal direction;

(b) SEQ ID NO:1 having mutations Leu 118Cys/Ala134Cys/Ser167Ala fused to SEQ ID NO:5 fused to SEQ ID NO: 4 having mutations Ser11Pro/Phe17Ala/Leu18Ala, fused in the N-terminal to C-terminal direction;

(c) SEQ ID NO:1 having mutations Leu 118 Cys/Ala134Cys/Ser167Ala fused to SEQ ID NO:5 fused to SEQ ID NO: 4 having mutations Ser11Pro/Asn80Ala, fused in the N-terminal to C-terminal direction;

(d) SEQ ID NO:1 having mutations Leu118Cys/Ala134Cys/Ser167Ala fused to SEQ ID NO:5 fused to SEQ ID NO: 4 having mutations Ser11Pro/Phe17Ala/Leu18Ala/Asn80Ala, fused in the N-terminal to C-terminal direction;

(e) SEQ ID NO: 1 having mutations Leu 118Cys/Ala134Cys/Ser167Ala fused to SEQ ID NO:6 fused to SEQ ID NO: 4 having mutation Ser11Pro, fused in the N-terminal to C-terminal direction;

(f) SEQ ID NO:1 having mutations Leu 118Cys/Ala134Cys/Ser167Ala fused to SEQ ID NO:6 fused to SEQ ID NO: 4 having mutations Ser11Pro/Phe17Ala/Leu18Ala, fused in the N-terminal to C-terminal direction;

(g) SEQ ID NO:1 having mutations Leu 118Cys/Ala134Cys/Ser167Ala fused to SEQ ID NO: 6 fused to SEQ ID NO: 4 having mutations Ser11Pro/Asn80Ala, fused in the N-terminal to C-terminal direction;

(h) SEQ ID NO:1 having mutations Leu118Cys/Ala134Cys/Ser167Ala fused to SEQ ID NO: 6 fused to SEQ ID NO: 4 having mutations Ser11Pro/Phe17Ala/Leu18Ala/Asn80Ala, fused in the N-terminal to C-terminal direction;

(i) SEQ ID NO:1 having mutations Leu 118Cys/Ala134Cys/Ser167Ala fused to SEQ ID NO: 7 fused to SEQ ID NO: 4 having mutation Ser11Pro, fused in the N-terminal to C-terminal direction;

(j) SEQ ID NO:1 having mutations Leu 118Cys/Ala134Cys/Ser167Ala fused to SEQ ID NO: 7 fused to SEQ ID NO: 4 having mutations Ser11Pro/Phe17Ala/Leu18Ala, fused in the N-terminal to C-terminal direction;

(k) SEQ ID NO: 1 having mutations Leu 118Cys/Ala134Cys/Ser167Ala fused to SEQ ID NO: 7 fused to SEQ ID NO: 4 having mutations Ser11Pro/Asn80Ala, fused in the N-terminal to C-terminal direction; and (l) SEQ ID NO: 1 having mutations Leu118Cys/Ala134Cys/Ser167Ala fused to SEQ ID NO: 7 fused to SEQ ID NO: 4 having mutations Ser11Pro/Phe17Ala/Leu18Ala/Asn80Ala, fused in the N-terminal to C-terminal direction.

* * * * *

SEQUENCE LISTING

```
<160> NUMBER OF SEQ ID NOS: 10

<210> SEQ ID NO 1
<211> LENGTH: 181
<212> TYPE: PRT
<213> ORGANISM: homo sapiens

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80
```

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 543
<212> TYPE: DNA
<213> ORGANISM: homo sapiens

<400> SEQUENCE: 2 cacccccatcc ctgactccag tcctctcctg caattcgggg gccaagtccg gcagcggtac    60
ctctacacag atgatgccca gcagacagaa gcccacctgg agatcaggga ggatgggacg   120 gtgggggggcg ctgctgacca gagccccgaa agtctcctgc agctgaaagc cttgaagccg   180
ggagttattc aaatcttggg agtcaagaca tccaggttcc tgtgccagcg gccagatggg   240
gccctgtatg gatcgctcca cttttgaccct gaggcctgca gcttccggga gctgcttctt   300
gaggacggat acaatgttta ccagtccgaa gcccacggcc tcccgctgca cctgccaggg   360
aacaagtccc cacaccggga ccctgcaccc cgaggaccag ctcgcttcct gccactacca   420
ggcctgcccc ccgcactccc ggagccaccc ggaatcctgg ccccccagcc ccccgatgtg   480
ggctcctcgg accctctgag catggtggga ccttcccagg gccgaagccc cagctacgct   540
tcc                                                                 543

<210> SEQ ID NO 3
<211> LENGTH: 232
<212> TYPE: PRT
<213> ORGANISM: homo sapiens

<400> SEQUENCE: 3

Ala Glu Pro Lys Ser Cys Asp Lys Thr His Thr Cys Pro Pro Cys Pro
1               5                   10                  15

Ala Pro Glu Lys Gly Gly Pro Ser Val Phe Leu Phe Pro Pro Lys Pro
            20                  25                  30

Lys Asp Thr Lys Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 4
<211> LENGTH: 230
<212> TYPE: PRT
<213> ORGANISM: homo sapiens
<220> FEATURE:
<221> NAME/KEY: MISC_FEATURE
<222> LOCATION: (11)..(11)
<223> OTHER INFORMATION: Xaa at position 11 = Pro or Ser
<220> FEATURE:
<221> NAME/KEY: MISC_FEATURE
<222> LOCATION: (16)..(16)
<223> OTHER INFORMATION: Xaa at position 16 = Pro or Glu
<220> FEATURE:
<221> NAME/KEY: MISC_FEATURE
<222> LOCATION: (17)..(17)
<223> OTHER INFORMATION: Xaa at position 17 = Phe, Val, or Ala
<220> FEATURE:
<221> NAME/KEY: MISC_FEATURE
<222> LOCATION: (18)..(18)
<223> OTHER INFORMATION: Xaa at position 18 = Leu, Glu, or Ala
<220> FEATURE:
<221> NAME/KEY: MISC_FEATURE
<222> LOCATION: (80)..(80)
<223> OTHER INFORMATION: Xaa at position 80 = Asn or Ala
<220> FEATURE:
<221> NAME/KEY: MISC_FEATURE
<222> LOCATION: (230)..(230)
<223> OTHER INFORMATION: Xaa at position 230 = Lys or is absent

<400> SEQUENCE: 4

Ala Glu Ser Lys Tyr Gly Pro Pro Cys Pro Xaa Cys Pro Ala Pro Xaa
1               5                   10                  15

Xaa Xaa Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
            35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Xaa
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
            115                 120                 125
```

```
Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Xaa
225                 230

<210> SEQ ID NO 5
<211> LENGTH: 15
<212> TYPE: PRT
<213> ORGANISM: homo sapiens

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 22
<212> TYPE: PRT
<213> ORGANISM: homo sapiens

<400> SEQUENCE: 6

Gly Ser Gly Gly Gly Gly Ser Gly Gly Gly Ser Gly Gly Gly Gly
1               5                   10                  15

Ser Gly Gly Gly Gly Ser
            20

<210> SEQ ID NO 7
<211> LENGTH: 30
<212> TYPE: PRT
<213> ORGANISM: homo sapiens

<400> SEQUENCE: 7

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 8
<211> LENGTH: 25
<212> TYPE: PRT
<213> ORGANISM: homo sapiens

<400> SEQUENCE: 8

Asp Ala Ala Ala Lys Glu Ala Ala Ala Lys Asp Ala Ala Ala Arg Glu
1               5                   10                  15

Ala Ala Ala Arg Asp Ala Ala Ala Lys
            20                  25

<210> SEQ ID NO 9
<211> LENGTH: 14
<212> TYPE: PRT
```

<213> ORGANISM: homo sapiens

<400> SEQUENCE: 9

```
Asn Val Asp His Lys Pro Ser Asn Thr Lys Val Asp Lys Arg
1               5                   10
```

<210> SEQ ID NO 10
<211> LENGTH: 585
<212> TYPE: PRT
<213> ORGANISM: homo sapiens

<400> SEQUENCE: 10

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
```

```
                 340             345             350
Tyr Glu Thr Thr Leu Glu Lys Cys Cys Ala Ala Asp Pro His Glu
            355             360             365

Cys Tyr Ala Lys Val Phe Asp Glu Phe Lys Pro Leu Val Glu Glu Pro
    370             375             380

Gln Asn Leu Ile Lys Gln Asn Cys Glu Leu Phe Glu Asn Leu Gly Glu
385             390             395             400

Tyr Lys Phe Gln Asn Ala Leu Leu Val Arg Tyr Thr Lys Lys Val Pro
                405             410             415

Gln Val Ser Thr Pro Thr Leu Val Glu Val Ser Arg Asn Leu Gly Lys
            420             425             430

Val Gly Ser Lys Cys Cys Lys His Pro Glu Ala Lys Arg Met Pro Cys
            435             440             445

Ala Glu Asp Tyr Leu Ser Val Val Leu Asn Gln Leu Cys Val Leu His
    450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
                485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
        515             520             525

Leu Val Glu Leu Val Lys His Lys Pro Lys Ala Thr Lys Glu Gln Leu
    530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585
```